United States Patent
Kim et al.

(10) Patent No.: US 11,480,511 B2
(45) Date of Patent: Oct. 25, 2022

(54) METHOD FOR ANALYZING DIFFUSION COEFFICIENT OF SOLVENT MOLECULES IN POLYMER MATERIAL

(71) Applicant: LG Chem, Ltd., Seoul (KR)

(72) Inventors: Seungha Kim, Daejeon (KR); In Hye Kwon, Daejeon (KR); Kyoung Hoon Kim, Daejeon (KR)

(73) Assignee: LG Chem, Ltd.

( * ) Notice: Subject to any disclaimer, the term of this patent is extended or adjusted under 35 U.S.C. 154(b) by 691 days.

(21) Appl. No.: 16/476,478

(22) PCT Filed: Aug. 6, 2018

(86) PCT No.: PCT/KR2018/008898
§ 371 (c)(1),
(2) Date: Jul. 8, 2019

(87) PCT Pub. No.: WO2019/035585
PCT Pub. Date: Feb. 21, 2019

(65) Prior Publication Data
US 2020/0056976 A1 Feb. 20, 2020

(30) Foreign Application Priority Data

Aug. 17, 2017 (KR) .................. 10-2017-0104326

(51) Int. Cl.
*G16C 60/00* (2019.01)
*G01N 15/08* (2006.01)
*G06F 17/11* (2006.01)

(52) U.S. Cl.
CPC ............. *G01N 15/08* (2013.01); *G06F 17/11* (2013.01); *G16C 60/00* (2019.02); *G01N 2015/086* (2013.01)

(58) Field of Classification Search
CPC ......... G16C 60/00; G06F 17/11; G01N 15/08; G01N 2015/086
See application file for complete search history.

(56) References Cited

U.S. PATENT DOCUMENTS

| | | | |
|---|---|---|---|
| 5,627,329 A | 5/1997 | Krishnan et al. | |
| 8,491,968 B2* | 7/2013 | Oki | B32B 37/24 427/372.2 |
| 2020/0056976 A1 | 2/2020 | Kim et al. | |

FOREIGN PATENT DOCUMENTS

| CN | 101907549 A | 12/2010 |
|---|---|---|
| CN | 106198594 A | 12/2016 |

(Continued)

OTHER PUBLICATIONS

Search report from International Application No. PCT/KR2018/008898, dated Nov. 27, 2018.

(Continued)

*Primary Examiner* — Nguyen Q. Ha
(74) *Attorney, Agent, or Firm* — Lerner, David, Littenberg, Krumholz & Mentlik, LLP

(57) ABSTRACT

The present invention provides a method for analyzing diffusion coefficients of solvent molecules in polymer materials by applying a diffusion coefficient analysis model using 4 descriptors related to solvent properties. The present invention can provide optimum solvents when it is necessary to screen solvents suitable for drying procedure in the preparation of polymer films using a solvent process or it is necessary to analyze the permeability of polymer materials used in the final products by effectively analyzing the diffusion coefficients of solvent molecules.

8 Claims, 2 Drawing Sheets

(56) References Cited

FOREIGN PATENT DOCUMENTS

| CN | 106501130 A | | 3/2017 | |
|---|---|---|---|---|
| EP | 3543679 A1 | | 9/2019 | |
| JP | 2015210119 A | | 11/2015 | |
| KR | 20110009914 A | | 1/2011 | |
| KR | 20190019437 A | | 2/2019 | |
| WO | 0102850 A1 | | 1/2001 | |
| WO | WO-2013117845 A1 | * | 8/2013 | ............. B01D 65/10 |

OTHER PUBLICATIONS

Mamaliga, Ioan, et al., "Measurements of sorption isotherms and diffusion coefficients by means of a magnetic suspension balance." Chemical Engineering and Processing, vol. 43, Received Jan. 21, 2003; accepted Mar. 15, 2003, pp. 753-763.

Reis, R. A., et al., "Diffusion Coefficients in Polymer-Solvent Systems for Highly Concentrated Polymer Solutions." Brazilian Journal of Chemical Engineering. Dec. 2001, vol. 18, No. 4, pp. 1-21.

Oishi, T., et al., "Estimation of Solvent Activities in Polymer Solutions Using a Group-Contribution Method." Industrial & Engineering Chemistry Process Design and Development, 1978, vol. 17, No. 3., pp. 333-339.

Zielinski, John, et al., "Predicting Polymer/Solvent Diffusion Coefficients Using Free-Volume Theory." AlChe Journal, Mar. 1992, vol. 28, No. 3, pp. 405-415.

Wibawa, Gede, et al., "Solubility of Seven Nonpolar Organic Solvents in Four Polymers Using the Piezoelectric-Quartz Sorption Method." Journal of Chemical and Engineering Data., Published on Web Apr. 11, 2002, vol. 47, No. 3, pp. 518-524.

Reis, R. A., et al., "Mutual Diffusion Coefficient Models for Polymer-Solvent Systems Based on the Chapman-Enskog Theory." Brazilian Journal of Chemical Engineering, Received: Feb. 13, 2003; Accepted: May 24, 2004, vol. 21, No. 4, pp. 611-619.

Luan, F., et al., "QSPR study of permeability coefficients through low-density polyethylene based on radial basis function neural networks and the heuristic method." Comutational Materials Science, vol. 37, Received Nov. 11, 2005; accepted Nov. 18, 2005, pp. 454-461.

Schabel, Wilhelm, et al., "Sorption and diffusion measurements in ternary polymer-solvent-solvent systems by means of a magnetic suspension balance-Experimental methods and correlations with a mofiied Flory-Huggins and free-volume theory." Chemical Engineering Science, vol. 62, Received Jun. 14, 2005; accepted Dec. 22, 2006 Availabe online Jan. 16, 2007, pp. 2254-2266.

Wong, Sim-Siong, et al., "Drying of semicrystalline polymers: mathematical modeling and experimental characterization of poly-(vinyl alcohol) films." Polymer, vol. 45, received Feb. 24, 204; accepted May 13, 2004; available online Jun. 5, 2004, pp. 5151-5161.

Kobuchi, et al., Measurement and Estimation of Mutual Diffusion Coefficients for Polymer-Solvent Systems Arithmetic, Journal of Material Physics, 1998, pp. 77-87, vol. 11, No. 2, Akita University, with English language abstract.

Yamamoto, et al., "Polycarbonate-Methylene Chloride System at 140o Diffusion Coefficient," Proceedings of Chemical Engineering, 1989, pp. 1038-1041, vol. 15, No. 5, with English language abstract.

Chang, L., "Molecular Simulation and Experimental Research on Simulating the Diffusion Behavior of Diesel Fuel Components in Polymer Membrane" China Journal, Jun. 2013, 3 pages.

Chinese Search Report for Application No. 201880004327.2 dated Apr. 13, 2021, pp. 1-4.

Vicente, M.S. et al., "Estimation of solvent activities in polymers solutions using a group-contribution method" Separation Purification Technology, Dec. 2001, pp. 671-679, vol. 22-23, Elsevier, Argentina.

Extended European Search Report for Application No. EP18846713.8 dated Jan. 2, 2020, 5 pgs.

R. Saure et al., "Drying of solvent-borne polymeric coatings: I. Modeling the drying process", Surface Coatings & Technology, vol. 99, No. 3, Feb. 23, 1998, pp. 253-256, XP005537566.

* cited by examiner

[FIG. 2]
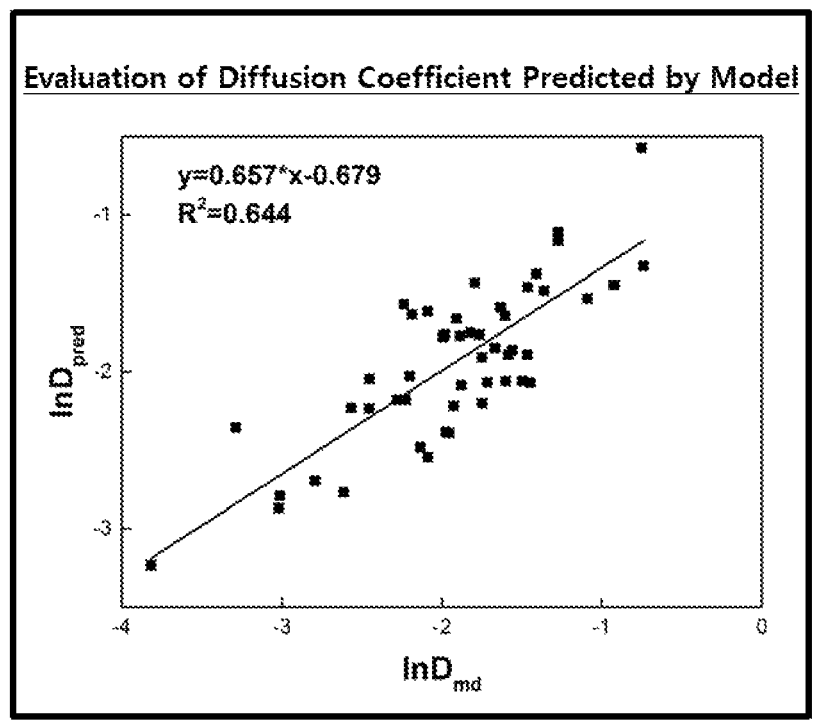

METHOD FOR ANALYZING DIFFUSION COEFFICIENT OF SOLVENT MOLECULES IN POLYMER MATERIAL

CROSS-REFERENCE TO RELATED APPLICATIONS

The present application is a national phase entry under 35 U.S.C. § 371 of International Application No. PCT/KR2018/008898 filed Aug. 6, 2018, which claims priority from Korean Patent Application No. 10-2017-0104326 filed Aug. 17, 2017, the disclosures of which are hereby incorporated by reference.

TECHNICAL FIELD

The present invention relates to a method for analyzing diffusion coefficients of residual solvent molecules in a polymer material for the preparation of a polymer film by a solution process.

BACKGROUND ART

The preparation of a polymer film, e.g., a color conversion film, by using a solution process needs a drying procedure for removing a solvent, thereby minimizing the amounts of a residual solvent in the polymer film, in order to enhance the durability of the polymer film. For this, the solvent molecule should have high mobility (see Wong et al, Polymer, 2004, 45, 5151; Schabel et al, Chem. Eng. Sci., 2007, 62, 2254).

Also, the polymer material used in pharmaceutical and electronic products need not to absorb moisture, oxygen, carbon dioxide and the like. To do this, it is necessary to analyze the permeability of the polymer film. The permeability of the polymer film is greatly influenced by the solubility and diffusion of the polymer material (see Luan et al, Comp. Mat. Sci., 2006, 37, 454). Thus, it is necessary to analyze a gas diffusion coefficient for each polymer material for the durability enhancement of the polymer film and the transmittance analysis of the final product.

The known method for analyzing a diffusion coefficient of a solvent molecule is to measure the diffusion coefficient of the solvent molecule in the polymer material through the experiments using magnetic suspension balance (MSB) and sorption equilibrium (see Mamaliga et al, Chem. Eng. & Proc., 2004, 43, 753). However, such method needs a Flory-Huggins parameter between the polymer material and the solvent molecule and it is difficult to reproduce the experiments. In addition, there is a limit of calculation time and the like in the measurement of a diffusion coefficient of a solvent molecule by using molecular dynamics.

Accordingly, it needs to develop an effective model for analyzing a diffusion coefficient of a solvent molecule for analysis of the drying property of a solvent during the preparation of a polymer film, and the gas permeability of a polymer film.

DETAILED DESCRIPTION OF THE INVENTION

Technical Problem

The object of the present invention is to provide a method for analyzing a diffusion coefficient of a solvent molecule in a polymer material by using a computer simulation model analyzed from a descriptors related to a solvent property.

Technical Solution

In order to accomplish the object of the present invention, the present provides a method for analyzing a diffusion coefficient of a solvent molecule in a polymer material for the preparation of a polymer film by using a solution process. Specifically, the method comprises analyzing the diffusion coefficient of the solvent molecule in the polymer material by using the diffusion coefficient analysis model of the following Equation 1:

$$\ln D_{pred} = c_1 \exp(-ME)[c_2 \ln EV + c_3 \ln NB + c_4 \ln MV + c_5] \quad \text{[Equation 1]}$$

wherein,

ME, EV, NB and MV are each a descriptor related to the solvent molecule,

ME is the mixing energy (kcal/mol) of the solvent molecule and the polymer material, EV is the enthalpy of vaporization (kcal/mol) of the solvent molecule, NB is the number of chemical bonds between solvent molecule elements, MV is the molar volume ($cm^3$/mol) of the solvent molecule, $c_1$ is an adjustment factor of 0 to 1, which is a value adjusted according to experiment conditions, $c_2$ is an adjustment factor of −10 to 0, which is a value related to EV weight of the solvent molecule and adjusted according to the polymer material, $c_3$ is an adjustment factor of −10 to 0, which is a value related to the NB between the solvent molecule elements and adjusted according to the polymer material, $c_4$ is an adjustment factor of −1 to 1, which is a value related to the MV of the solvent molecule and adjusted according to the polymer material, $c_5$ is an adjustment factor of −10 to 10, which is a value used when weighing drying-relevant properties including heat of vaporization and solvent volume as compared with the solubility between the solvent molecule and the polymer material, and adjusted according to the polymer material.

In one embodiment, the diffusion coefficient ($\ln D_{pred}$) of the solvent molecule calculated from the diffusion coefficient analysis model of Equation 1 are in correlation with a diffusion coefficient ($\ln D_{md}$) of the solvent molecule analyzed via molecular dynamics by applying an NPT isothermal-isobaric ensemble, and the value $R^2$ of root mean square deviation (RMSD) for the correlation may range from 0.6 to 0.99.

In one embodiment, the diffusion coefficient analysis model of Equation 1 may be obtained by analyzing, via molecular dynamics, the diffusion coefficient ($\ln D_{md}$) of various kinds of a solvent molecule in a certain polymer material under specific temperature and pressure conditions; and performing multi-linear regression by using descriptors ME, EV, NB and MV related to the solvent molecule in order to give the adjustment factors for the diffusion coefficient analysis model of Equation 1. According to the above, via molecular dynamics, the diffusion coefficient analysis model with descriptors related to the solvent molecule may be obtained to predict the diffusion coefficients.

Advantageous Effects

The present invention can provide an optimum solvent when it is necessary to screen a solvent suitable for a drying process in the preparation of a polymer film by using a solvent process or it is necessary to analyze the permeability of a polymer material used in the final product by effectively analyzing a diffusion coefficient of a solvent molecule.

BRIEF DESCRIPTION OF THE DRAWINGS

FIG. 2 is a graph showing correlation of the diffusion coefficient of the solvent molecule analyzed via molecular dynamics and the diffusion coefficient of the solvent molecule calculated by using the diffusion coefficient analysis model of Equation 1.

BEST MODE

Figure 1:
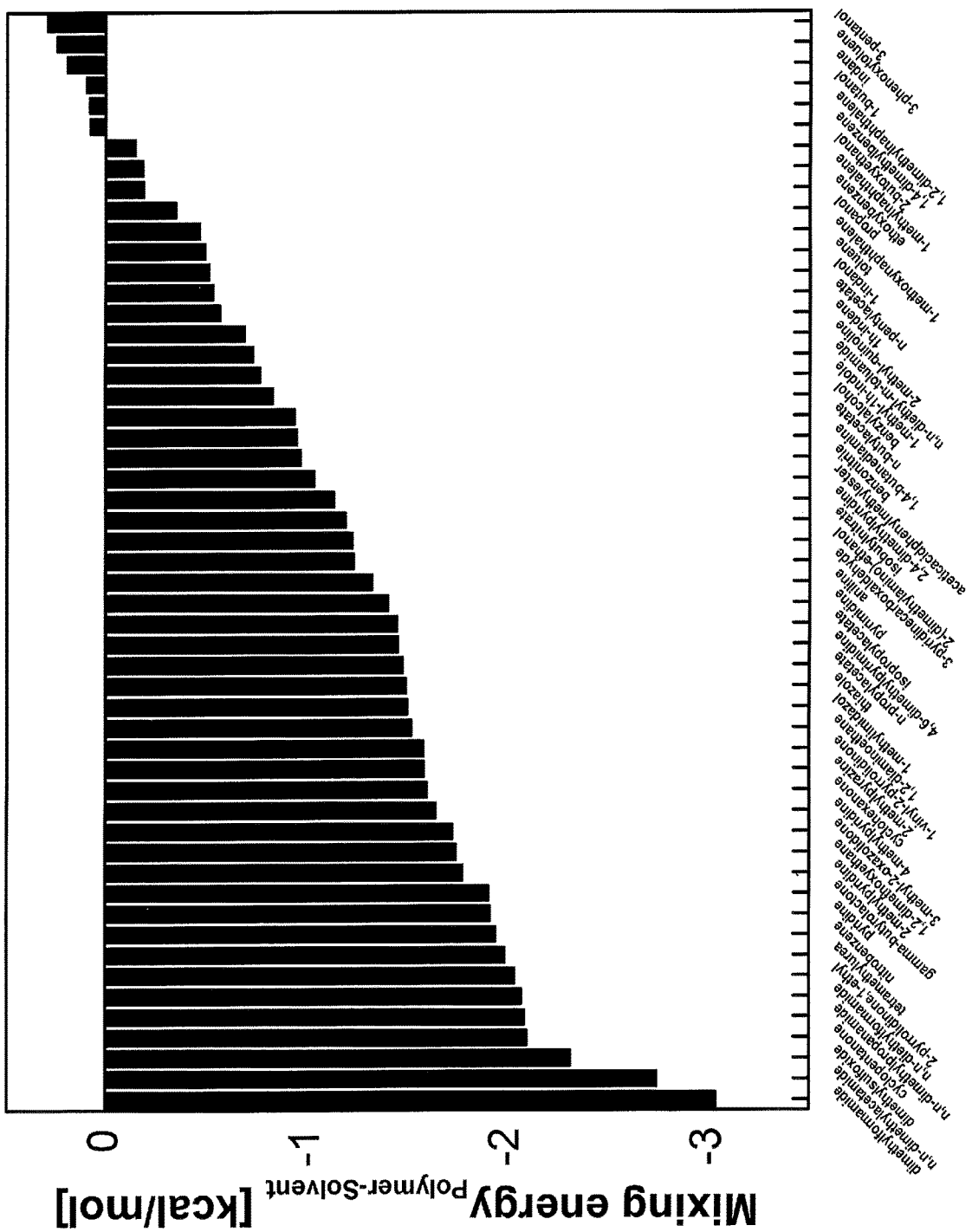
FIG. 1 shows the analysis results for mixing energy (ME) of the solvent molecule the polymer material obtained by the COSMO-RS theory.

The present invention may have various variations and embodiments, and the present invention will be described in detail referring to specific working examples and figures. However, it should be understood that the description proposed herein is just a preferable example for the purpose of illustrations only, not intended to limit the scope of the invention, so it should be understood that other equivalents and modifications could be made thereto without departing from the spirit and scope of the invention. Meanwhile, the description of the well-known functions or constructions may be omitted if it would obscure the subject matter of the present invention.

The present invention is to analyze a diffusion coefficient of a solvent molecule in order to minimize the amounts of a residual solvent in a polymer film after the preparation of the polymer film or detect the permeability of the polymer film, and provides a computer simulation model to analyze the diffusion coefficient of the solvent molecule by using a descriptors related to solvent properties.

Specifically, the present invention provides a method for analyzing a diffusion coefficient of a solvent molecule in a polymer material for the preparation of a polymer film by using a solution process and it is applicable in analyzing the permeability of the polymer film. The method comprises analyzing the diffusion coefficient of the solvent molecule in the polymer material by using the diffusion coefficient analysis model of the following Equation 1:

$$\ln D_{pred} = c_1 \exp(-ME)[c_2 \ln EV + c_3 \ln NB + c_4 \ln MV + c_5]$$ [Equation 1]

wherein,

ME, EV, NB and MV are each a descriptor related to the solvent molecule,

ME is the mixing energy (kcal/mol) of the solvent molecule and the polymer material, EV is the enthalpy of vaporization (kcal/mol) of the solvent molecule, NB is the number of chemical bonds between solvent molecule elements, MV is the molar volume ($cm^3$/mol) of the solvent molecule, $c_1$ is an adjustment factor of 0 to 1, which is a value adjusted according to experiment conditions, $c_2$ is an adjustment factor of −10 to 0, which is a value related to EV weight of the solvent molecule and adjusted according to the polymer material, $c_3$ is an adjustment factor of −10 to 0, which is a value related to the NB between the solvent molecule elements and adjusted according to the polymer material, $c_4$ is an adjustment factor of −1 to 1, which is a value related to the MV of the solvent material and adjusted according to the polymer material, $c_5$ is an adjustment factor of −10 to 10, which is a value used when weighing drying-relevant properties including heat of vaporization and solvent volume as compared with the solubility between the solvent molecule and the polymer material, and adjusted according to the polymer material.

In one embodiment, the ME of the solvent molecule and the polymer material may be obtained by the COSMO-RS theory.

In the present invention, the model of analyzing the diffusion coefficient of the solvent molecule for the polymer material, e.g., a polymer binder or a polymer resins may be obtained as follows.

First, the diffusion coefficient of various kinds of the solvent molecule, e.g., 50 or more kinds of the solvent molecule as shown in FIG. 1, on a certain polymer material is analyzed via a molecular dynamic program that is a high-level calculation method. The molecular dynamic program is used in the specific temperature and pressure condition (e.g., 150° C. and 1 atm), and the diffusion coefficient ($\ln D_{md}$) of each solvent molecule may be analyzed by applying an NPT isothermal-isobaric ensemble. Examples of the molecular dynamic program may include FORCITE, GROMACS, LAMMPS, etc.

With respect to the diffusion coefficient of the solvent molecule analyzed by molecular dynamics, a multi-linear regression may be performed by using 4 descriptors, i.e., ME, EV, NB and MV in order to give the adjustment factors for the diffusion coefficient analysis model of Equation 1, and the diffusion coefficient ($\ln D_{pred}$) of the solvent molecule may be calculated from such an analysis model.

Then, the values of the 4 descriptors may be used for effectively analyzing the diffusion coefficient of the solvent molecule in the polymer material by using the diffusion coefficient analysis model of Equation 1, even though the molecular dynamic analysis is not applied. By using such an analysis model, the present invention can more efficiently select the solvent molecule suitable for the preparation of the polymer material and the improvement of the properties the final product, such as durability and permeability.

The diffusion coefficient ($\ln D_{pred}$) of the solvent molecule calculated by using the diffusion coefficient analysis model of Equation 1 are in correlation with the diffusion coefficient ($\ln D_{md}$) of the solvent molecule analyzed via molecular dynamics by applying the NPT isothermal-isobaric ensemble. In one embodiment, the value $R^2$ of root mean square deviation (RMSD) for the correlation of the $\ln D_{pred}$ and the $\ln D_{md}$ may range from 0.6 to 0.99, for example 0.64 to 0.8.

In one embodiment, the solvent molecule suitable in such analysis model is not particularly limited if they are generally used in the preparation of a product from the polymer material. For example, the solvent molecule may be selected from the group consisting of xylene, acetone, chloroform, methyl ethyl ketone (MEK), methyl isobutyl ketone (MIRK), ethyl acetate (EA), butyl acetate, cyclohexanone, propylene glycol methyl ethyl acetate (PGMEA), dioxane, N-methylpyrrolidone (NMP), dimethylformamide (DMF), N,N-dimethylacetamide, dimethylsulfoxide, cyclopentanone, N,N-dimethylpropanamide N,N-diethylformamide, 1-ethyl-2-pyrrolidinone, tetramethylurea, nitrobenzene, pyridine, γ-butyrolactone, methylpyridine, 2-dimethoxyethane, 3-methyl-2-oxazolidone, 4-methylpyridine, cyclohexanone, 2-methylpyrazine, 1-vinyl-2-pyrrolidinone, 1,2-diaminoethane, 1-methylimidazole, thiazole, n-propyl acetate, 4,6-dimethylpyrimidine, isopropyl acetate, pyrimidine, aniline, 3-pyridinecarboxaldehyde, 2-(dimethylamino)-ethanol, isobutyl nitrate, 2,4-dimethylpyridine, phenyl methyl acetate, benzonitrile, 1,4-butanediamine, n-butyl acetate, benzyl alcohol, 1-methyl-1H-indole, N, N-diethyl-m-toluamide, 2-methyl-quinoline, 1H-indene, n-pentyl acetate, 1-indanol, toluene, 1-methoxynaphthalene, propanol, ethoxybenzene, 1-methylnaphthalene, 2-butoxyethanol, 1,4-dimethylbenzene, 1,2-dimethylnaphthalene, 1-butanol, indan, 3-phenoxy toluene, 3-pentanol, and a mixture of two or more thereof.

In one embodiment, the polymer material suitable in such analysis model may be a polymer binder or a polymer resin having thermoplastic or thermosetting properties, for example, polyolefins, acrylates, polyurethanes, polyethers, polyesters, polyamides, formaldehyde and silicone polymers, or copolymers obtained from two or more monomers contained these polymers. These may be used alone or in combination of two or more. Specific examples of the polymer may include polyethylene (PE), polyvinyl fluoride (PVF), polyvinyl chloride (PVC), polyvinylidene fluoride (PVDF), polyvinylidene chloride (PVDC), polychlorotrifluoroethylene (PCTFE), polytetrafluoroethylene(PTFE), polypropylene (PP), ethylene vinyl acetate (EVA), polymethyl methacrylate (PMMA), poly(1-butene), poly(4-methylpentene), polystyrene, polyvinylpyridine, polybutadiene, polyisoprene polychloroprene, styrene-acrylonitrile copolymer (SAN) acrylonitrile-butadiene-styrene terpolymer, ethylene-methacrylic acid copolymer, styrene-butadiene rubber, nitrile rubber, tetrafluoroethylene copolymer, polyacrylate, polymethacrylate, polyacrylamide, polyvinyl acetate, polyvinyl alcohol, polyvinyl butyral, polyvinyl ether, polyvinyl pyrrolidone, polyvinyl carbazole, polyurethane, polyacetal, polyethylene glycol, polypropylene glycol, epoxy resins, polyphenylene oxide, polyethylene terephthalate, polybutylene terephthalate, polydihydroxymethyl cyclohexyl terephthalate, cellulose ester, polycarbonate, polyimide, polyimide, polyarylene, etc., but the present invention is not limited thereto.

In one embodiment, the diffusion coefficient analysis may be performed at a temperature of 10° C. to 200° C. and a pressure of 1 atm to 3 atms.

Hereinafter, the present invention will be described in more detail with reference to Examples. It will be apparent to those skilled in the art that the following examples are intended to be illustrative of the present invention and not to be construed as limiting the scope of the invention.

EXAMPLES

The diffusion coefficient of solvent molecule in a polymer binder were analyzed for the purpose of minimizing a residual solvent in a film during a drying procedure for the preparation of the film, as follows.

(1) The diffusion coefficient ($lnD_{md}$) at room temperature of 50 kinds of the solvent molecule as shown in FIG. 1 on polymethyl methacrylate (PMMA) as a polymer binder were analyzed via a molecular dynamic programs (packages of FORCITE, GROMACS, LAMMPS) that is a high-level calculation method.

(2) The dynamic programs produced a simulation box in which the solvent molecule was each optionally positioned and was used in an amount of 20 wt % based on the weight of the polymer binder.

(3) An NPT isothermal-isobaric ensemble was applied under the conditions of 150° C. and 1 atm to analyze the diffusion coefficient of each solvent.

(4) A multi-linear regression was performed by using 4 descriptors, i.e., ME, EV, NB and MV of the diffusion coefficient analysis model of Equation 1 to give the adjustment factors ($c_1$, $c_2$, $c_3$, $c_4$ and $c_5$), specifically $c_1$:0.881, $c_2$: −1.643, $c_3$: −2.069, $c_4$: 0.896 and $c_5$: 5.639. The mixing energy (ME) of each solvent molecule and the polymer material was obtained by using the COSMO-RS theory. The results thereof were shown in FIG. 1

The correlation of the diffusion coefficient ($lnD_{pred}$) of the solvent molecule analyzed in the above and the diffusion coefficient ($lnD_{md}$) of the solvent molecule analyzed via molecular dynamics was shown in FIG. 2. The correlation of the $lnD_{pred}$ and the $lnD_{md}$ was represented by the following Equation 2, and the value $R^2$ of RMSD for the correlation of the $lnD_{pred}$ and the $lnD_{md}$ was 0.644

$$y=0.657x-0.679 \quad R^2=0.644 \quad \text{[Equation 2]}$$

From the value of RMSD, the diffusion coefficient of the solvent molecule obtained by using the diffusion coefficient analysis model according to the present invention can be confirmed to be highly accurate as there was little difference between the diffusion coefficient analyzed by the present invention and those analyzed via the molecular dynamics. Accordingly, the diffusion coefficient analysis model of the present invention can be used to efficiently select a solvent suitable in the field of a displays, a backlight units and an illuminator devices which need the improvement of polymer properties, even though the molecular dynamic analysis is not applied.

While the present invention has been particularly shown and described with reference to figures and embodiments thereof, it will be understood by those of ordinary skill in the art that the scope of the present invention is not limited thereby and that various changes and modifications may be made therein. Therefore, the actual scope of the present invention will be defined by the appended claims and their equivalents.

What is claimed is:

1. A method for analyzing a diffusion coefficient of a solvent molecule in a polymer material for preparation of a polymer film by using a solution process, comprising:
analyzing the diffusion coefficient of the solvent molecule in the polymer material by using the diffusion coefficient analysis model of the following Equation 1:

$$lnD_{pred}=c_1 \exp(-ME)[c_2 \ lnEV+c_3 \ lnNB+c_4 \ lnMV+c_5] \quad \text{[Equation 1]}$$

wherein,
ME, EV, NB and MV are each a descriptor related to the solvent molecule,
ME is the mixing energy (kcal/mol) of the solvent molecule and the polymer material,
EV is the enthalpy of vaporization (kcal/mol) of the solvent molecule,
NB is the number of chemical bonds between solvent molecule elements,
MV is the molar volume (cm$^3$/mol) of the solvent molecule,
$c_1$ is an adjustment factor of 0 to 1, which is a value adjusted according to experiment conditions,
$c_2$ is an adjustment factor of −10 to 0, which is a value related to EV weight of the solvent molecule and adjusted according to the polymer material,
$c_3$ is an adjustment factor of −10 to 0, which is a value related to the NB between the solvent molecule elements and adjusted according to the polymer material, $c_4$ is an adjustment factor of −1 to 1, which is a value related to the MV of the solvent molecule and adjusted according to the polymer material, $c_5$ is an adjustment factor of −10 to 10, which is a value used when weighing drying-relevant properties including heat of vaporization and solvent volume as compared with the solubility between the solvent molecule and the polymer material, and adjusted according to the polymer material.

2. The method of claim 1, wherein the diffusion coefficient ($lnD_{pred}$) of the solvent molecule calculated from the diffusion coefficient analysis model of Equation 1 is in correlation with a diffusion coefficient ($lnD_{md}$) of the solvent molecule analyzed via molecular dynamics by applying an NPT isothermal-isobaric ensemble, and the value $R^2$ of root mean square deviation (RMSD) for the correlation ranges from 0.6 to 0.99.

3. The method of claim 1, wherein the solvent molecule is selected from the group consisting of xylene, acetone, chloroform, methyl ethyl ketone (MEK), methyl isobutyl ketone (MIBK), ethyl acetate (EA), butyl acetate, cyclohexanone, propylene glycol methyl ethyl acetate (PGMEA), dioxane, N-methylpyrrolidone (NMP), dimethylformamide (DMF), N,N-dimethylacetamide, dimethylsulfoxide, cyclopentanone, N,N-dimethylpropanamide, N,N-diethylformamide, 1-ethyl-2-pyrrolidinone, tetramethylurea, nitrobenzene, pyridine, γ-butyrolactone, 2-methylpyridine, 1,2-dimethoxyethane, 3-methyl-2-oxazolidone, 4-methylpyridine, cyclohexanone, 2-methylpyrazine, 1-vinyl-2-pyrrolidinone, 1,2-diaminoethane, 1-methylimidazole, thiazole, n-propyl acetate, 4,6-dimethylpyrimidine, isopropyl acetate, pyrimidine, aniline, 3-pyridinecarboxaldehyde, 2-(dimethylamino)-ethanol, isobutyl nitrate, 2,4-dimethylpyridine, phenyl methyl acetate, benzonitrile, 1,4-butanediamine, n-butyl acetate, benzyl alcohol, 1-methyl-1H-indole, N,N-diethyl-m-toluamide, 2-methyl-quinoline, 1H-indene, n-pentyl acetate, 1-indanol, toluene, 1-methoxynaphthalene, propanol, ethoxybenzene, 1-methylnaphthalene, 2-butoxyethanol, 1,4-dimethylbenzene, 1,2-dimethylnaphthalene, 1-butanol, indan, 3-phenoxy toluene, 3-pentanol, and a mixture of two or more thereof.

4. The method of claim 1, wherein the polymer material is selected from the group consisting of polyethylene (PE), polyvinyl fluoride (PVF), polyvinyl chloride (PVC), polyvinylidene fluoride (PVDF), polyvinylidene chloride (PVDC), polychlorotrifluoroethylene (PCTFE), polytetrafluoroethylene (PTFE), polypropylene (PP), ethylene vinyl acetate (EVA), polymethyl methacrylate (PMMA), poly(l-butene), poly(4-methylpentene), polystyrene, polyvinylpyridine, polybutadiene, polyisoprene, polychloroprene, styrene-acrylonitrile copolymer (SAN), acrylonitrile-butadiene-styrene terpolymer, ethylene-methacrylic acid copolymer, styrene-butadiene rubber, nitrile rubber, tetrafluoroethylene copolymer, polyacrylate, polymethacrylate, polyacrylamide, polyvinyl acetate, polyvinyl alcohol, polyvinyl butyral, polyvinyl ether, polyvinyl pyrrolidone, polyvinyl carbazole, polyurethane, polyacetal, polyethylene glycol, polypropylene glycol, epoxy resins, polyphenylene oxide, polyethylene terephthalate, polybutylene terephthalate, polydihydroxymethyl cyclohexyl terephthalate, cellulose ester, polycarbonate, polyamide, polyimide, and polyarylene.

5. The method of claim 1, which is performed at a temperature of 10° C. to 200° C. and a pressure of 1 atm to 3 atms.

6. The method of claim 1, wherein analyzing the diffusion coefficient of the solvent molecule in the polymer material is performed without using molecular dynamics software.

7. A method of producing a diffusion coefficient analysis model for analyzing a diffusion coefficient of a solvent molecule in a polymer material comprising:

analyzing the diffusion coefficient ($lnD_{md}$) of a solvent molecule on a polymer material using molecular dynamics software, comprising:

producing a simulation box in which the solvent molecule was positioned and was used in an amount of 20 wt % based on the weight of the polymer material, and applying an NPT isothermal-isobaric ensemble at a temperature condition and a pressure condition to analyze the diffusion coefficient of the solvent molecule; and performing multi-linear regression by using ME, EV, NB and MV in order to give the adjustment factors $c_1$, $c_2$, $c_3$, $c_4$, and $c_5$ for the diffusion coefficient analysis model of Equation 1:

$$lnD_{pred}=c_1 \exp(-ME)[c_2 \ln EV + c_3 \ln NB + c_4 \ln MV + c_5] \quad \text{[Equation 1]}$$

wherein,

ME, EV, NB and MV are each a descriptor related to the solvent molecule,

ME is the mixing energy (kcal/mol) of the solvent molecule and the polymer material, EV is the enthalpy of vaporization (kcal/mol) of the solvent molecule, NB is the number of chemical bonds between solvent molecule elements, MV is the molar volume (cm$^3$/mol) of the solvent molecule, $c_1$ is an adjustment factor of 0 to 1, which is a value adjusted according to experiment conditions, $c_2$ is an adjustment factor of −10 to 0, which is a value related to EV weight of the solvent molecule and adjusted according to the polymer material, $c_3$ is an adjustment factor of −10 to 0, which is a value related to the NB between the solvent molecule elements and adjusted according to the polymer material, $c_4$ is an adjustment factor of −1 to 1, which is a value related to the MV of the solvent molecule and adjusted according to the polymer material, $c_5$ is an adjustment factor of −10 to 10, which is a value used when weighing drying-relevant properties including heat of vaporization and solvent volume as compared with the solubility between the solvent molecule and the polymer material, and adjusted according to the polymer material.

8. The method of claim 7, wherein the temperature condition is 150° C. and the pressure condition is 1 atm.

* * * * *